United States Patent [19]

DuBois

[11] 4,348,333
[45] Sep. 7, 1982

[54] β-KETOCARBOXYL AND PHOSPHONATE DIHYDRO-CHALCONE SWEETENERS

[75] Inventor: Grant E. DuBois, Palo Alto, Calif.

[73] Assignee: The United States of America as represented by the Secretary of the Department of Health and Human Services, Washington, D.C.

[21] Appl. No.: 310,406

[22] Filed: Oct. 9, 1981

[51] Int. Cl.³ .................. C07F 9/38; C07C 57/38; A23L 1/236
[52] U.S. Cl. .................. 260/502.4 R; 562/464; 426/548
[58] Field of Search .................. 562/464; 260/502.4 R

[56] References Cited

U.S. PATENT DOCUMENTS

| | | | |
|---|---|---|---|
| 3,032,578 | 5/1962 | MacMullen et al. | 260/502.4 R |
| 3,293,176 | 12/1966 | White | 260/502.4 R |
| 3,751,270 | 8/1973 | Rizzi | |
| 3,828,030 | 8/1974 | Kinugasa et al. | |
| 3,855,301 | 12/1974 | Rizzi | |
| 3,956,375 | 5/1976 | Farkas et al. | |
| 3,965,147 | 6/1976 | Hendricks | 260/502.4 R |
| 3,974,299 | 8/1976 | Crosby et al. | |
| 3,976,687 | 8/1976 | Crosby et al. | 562/464 |
| 3,976,790 | 8/1976 | Crosby et al. | |
| 4,055,678 | 10/1977 | Crosby et al. | |
| 4,226,804 | 10/1980 | DuBois et al. | |

Primary Examiner—Joseph E. Evans
Attorney, Agent, or Firm—Holman & Stern

[57] ABSTRACT

Dihydrochalcones of the formula

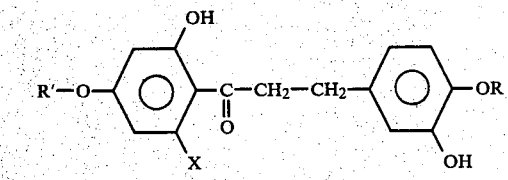

are disclosed wherein $M^+$ is a physiologically acceptable cation, X is H or OH, R is a lower alkyl and R' is

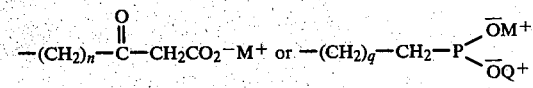

and n and q, respectively, may have a numerical value of 1 to 6. These materials are useful as sweeteners for edibles.

14 Claims, No Drawings

β-KETOCARBOXYL AND PHOSPHONATE DIHYDRO-CHALCONE SWEETENERS

BACKGROUND OF THE INVENTION

1. Field of the Invention

This invention concerns synthetic sweeteners. More particularly, it concerns a new group of substituted dihydrochalcone compounds, their use as sweeteners for edible compositions such as foodstuffs, and certain amino dihydrochalcone intermediates.

2. Description of the Prior Art

Dihydrochalcones are compounds having a

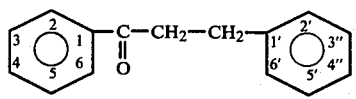

basic structure. A number of such compounds, both natural and synthetic, have been disclosed in the prior art. These materials vary from one another by the nature and placement of substituents on the aromatic rings.

In 1963, dihydrochalcones took an increased importance when it was discovered that some, but by no means all, of their number are sweet (Horowitz and Gentili, U.S. Pat. No. 2,087,871, issued Apr. 30, 1963). The earliest examples of sweet dihydrochalcones were derived from naturally occurring materials (flavanones) having saccharide residues attached at position four. More recently, applicants, their coworkers, and others have disclosed several sweet dihydrochalcones having smaller and simpler substituents at their four positions as evidenced by: Rizzi, U.S. Pat. No. 3,855,301, issued Dec. 17, 1974; Rizzi, U.S. Pat. No. 3,751,270, issued Aug. 7, 1973; Ibaraki, et al., U.S. Pat. No. 3,828,030, issued Aug. 6, 1974; Farkus et al., U.S. Pat. No. 3,956,375, issued May 11, 1976; Crosby et al., U.S. Pat. No. 3,974,299, issued Aug. 10, 1976; Crosby et al., U.S. Pat. No. 4,055,678, issued Oct. 25, 1977; DuBois et al., U.S. Pat. No. 4,336,804, issued Oct. 1, 1980; as well as pending United States patent application Ser. No. 19,054, which shows dihydrochalcones having an amino acid type structure at their 4 position.

This work has repeatedly confirmed the empirical nature of the taste-chemical structure relationship. The exact nature of substituents and their placement on the molecule are critical. A change which is minor on its face may have a major effect on the taste properties of the dihydrochalcone. Two taste-related major goals of dihydrochalcone sweetener research are: (1) To provide compounds having solubility in aqueous media adequate to form suitably sweet consumer products; and (2) To eliminate, or at least minimize, the menthol-like aftertaste and prolonged sweet aftertastes which have plagued many of the dihydrochalcones prepared heretofore. The present invention seeks to realize these goals.

SUMMARY OF THE INVENTION

We have now discovered a group of new dihydrochalcones which have attractive sweetener properties. These materials, which are classified as β-ketocarboxylate and phosphonate dihydrochalcones, are represented structurally as shown in General Formulas Ia and Ib

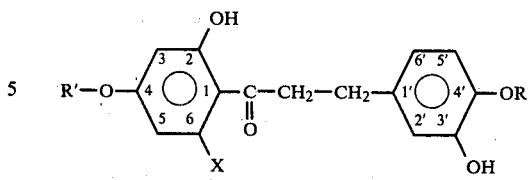

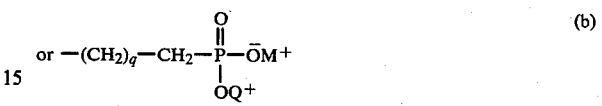

where R' is $-(CH_2)_n-\overset{O}{\overset{\|}{C}}-CH_2CO_2^-M^+$ (a)

or $-(CH_2)_q-CH_2-\overset{O}{\overset{\|}{\underset{\underset{OQ^+}{|}}{P}}}-\bar{O}M^+$ (b)

and n and q, respectively, may have a numerical value of 1 to 5 wherein R is a lower alkyl of from 1 to 3 carbons inclusive, X is hydrogen or hydroxy, and M+ is a physiologically acceptable cation as is Q+.

These materials may be named 2,3',6-trihydroxy and 2,3'-dihydroxy-4(oxo-carboxyalkoxy)-4'-alkoxydihydrochalcones, and 2,3',6-trihydroxy and 2,3'-dihydroxy-4(phosphoalkoxy)-4'-alkoxydihydrochalcones, respectively, and salts thereof. These materials impart sweet flavors to foods, beverages, medicaments and other comestibles.

DETAILED DESCRIPTION OF THE INVENTION

The Compounds

The compounds of the present invention have the structure shown in General Formula I. In that formula, R is an alkyl, more particularly a 1, 2, or 3 carbon alkyl that preferably is linear, i.e., methyl, ethyl or n-propyl. Methyl is the most preferred R group.

X is either hydrogen or hydroxy, with hydroxy being preferred. M+ and Q+ are physiologically acceptable cations. As used herein, a "physiologically acceptable cation" is defined to include hydrogen, ammonium and the cations of the third and fourth period metals which are nontoxic, i.e., Na(I), K(I), Mg(II), Ca(II), Mn(II), Al(III), and Zn(II). Preferred cations include hydrogen and cations of the third and fourth period group I and II metals, i.e., Na(I), K(I), Mg(II), and Ca(II), with K, Na and H being the most preferred cations. In the structural formulae of this specification and claims, the divalent calcium cation will be shown as ½ Ca++ to indicate a charge balance in the instance of the monovalent carboxyl group while the Ca++ or ½ Ca++ will be used to illustrate a fully satisfied charge or the acid salt, respectively, in the instance of the phosphonate salts. Other polyvalent cations will be shown similarly.

In actual practice, with the exception of the divalent group in which both hydrogen atoms have been displaced, the Ca++ is associated with two monovalent dihydrochalcone groups. The most preferred compounds are those materials illustrated by Formula I, wherein R is —CH3, M+ is K+ or Na+, Q+ is H+ and X is —OH. In the phosphonate derivatives, practical considerations of solubility and pH, make the acid salts, that is, those compounds in which Q+ is hydrogen while M+ is another physiologically acceptable cation, most preferable.

The numerical value of both n and q lie within the range of 1 to 5. Subjective taste testing has indicated that both n and q are preferably between 1 and 3, with 1 being most preferred for n. The most preferred value of q is 2.

Preparation of Dihydrochalcones Having β-Ketocarboxyl Substituents

The materials of General Formula $I_a$ may be conveniently formed according to the general scheme.

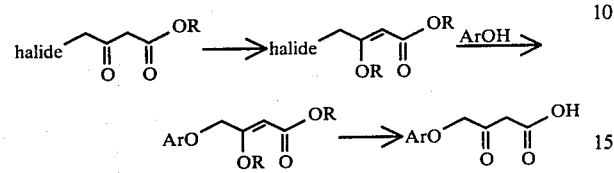

where Ar represents the flavanones shown in General Formula II

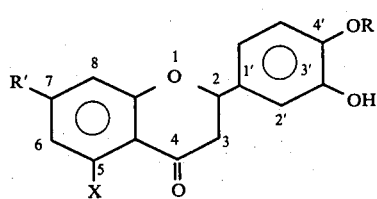

and substitution occurs at the 7-position.

Reaction proceeds with an appropriate alkylating agent, such as an organic halide and specifically a lower alkyl ester of β-methoxy-terminal halo-α,β-unsaturated carboxylic acids the methyl or ethyl ester and the iodo- or bromo-derivatives being most preferred. A suitable polar, aprotic (nonhydroxyl) reaction medium is employed in the alkylation step. Flavanones having protecting groups to avoid undesirable reaction with hydroxy groups other than at the 7-position may be initially prepared. Thereafter, the flavanone may be opened to the desired dihydrochalcone configuration. The flavanones of Formula II include hesperetin and its X equals hydrogen and its R equals $C_2H_5$ and $C_3H_7$ equivalents.

This preparative scheme may be illustrated by the following reaction equations, which are to be considered solely exemplary and in no way limiting.

Step A

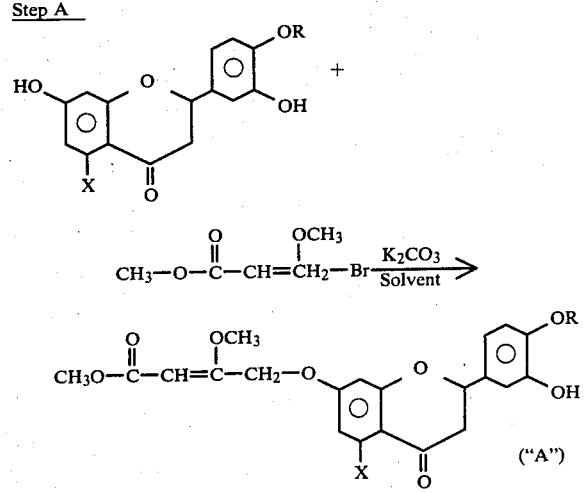

Step B $$\text{"A"} \xrightarrow[\text{Catalyst}]{\text{MOH} \atop H_2}$$

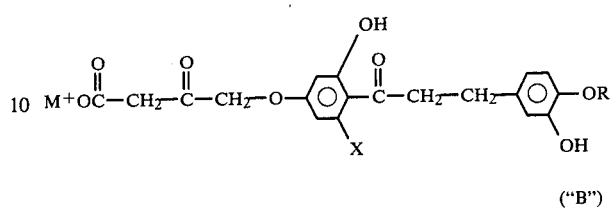

("B")

The substitution reaction of the conjugated ester with the flavanone 7-position (Step A, above) is carried out as follows.

Freshly prepared lower alkyl ester of β-methoxy-terminal halo-α,β-unsaturated carboxylic acid and the flavanone are combined in a liquid phase polar aprotic reaction medium. Suitable media include N,N-dimethylformamide (DMF), dimethylsulfoxide, hexamethylphosphoramide, N-methylpyrolidone, acetone and the like with DMF generally being preferred. The molar amounts of flavanone and ester are about equal with moderate excesses of the ester, i.e., 1 to 3, preferably 1 to 2 and most preferably 1 to 1.5 equivalents per mole of flavanone being preferred. The ester can be added in stages, if desired.

An acid acceptor, such as an alkali metal carbonate, bicarbonate or hydroxide, and preferably $Na_2CO_3$ or $K_2CO_3$, is present during the alkylation reaction. This material is generally present in a molar amount about equal to the moles of flavanone—i.e., 1–1.5 equivalents, based on flavanone. The reaction is carried out under low to moderate temperatures. Generally, the reaction temperature should be maintained at or below room temperature, such as $-10°$ C. to $45°$ C. and preferably $0°$ C. to $30°$ C. is employed and requires relatively long reaction times such as from 10 to 160 hours and preferably 15 to 140 hours to complete. It is preferred that the reaction mixture be stirred, while protected from light, for several hours at the lower end of the preferred temperature range before being allowed to warm to approximately ambient temperature. At $30°$ C., $30\pm\%$ reaction occurs in 24–30 hours.

The product of Step A is recovered from the reaction product by conventional workup such as by evaporation of solvent, followed by trituration of the residue with aqueous mineral acid or acid treatment of the residue in a suitable solvent and extraction with ethylacetate, chloroform, or the like, and evaporation to dryness of the organic phase containing the flavanone as an oil. The flavanone may be subsequently purified by column chromatography and recrystallized to obtain crystals of pure material.

The opening and hydrogenation of the flavanone to the dihydrochalcone and concomitant removal of any protecting groups which may be present (Step B, above) are carried out in one step with molecular hydrogen, base and a suitable catalyst. Mild conditions are employed, such as a gross excess of hydrogen (for example, 10 to 100 psi), dilute aqueous base such as 0.2 to 8 molar, preferably 0.4 to 4 molar alkali metal hydroxide, particularly KOH or NaOH and a noble metal catalyst such as palladium or platinum (preferably palladium), preferably supported such as upon charcoal or the like. Times of from a few hours (such as 3 hours) to about 60 hours, with temperatures of from room temperature (20° C.) to say 35° C. may be employed.

Following hydrogenation and opening, the substituted dihydrochalcone product may be recovered, such as by filtration, neutralization, evaporation to dryness and chromatography, such as by liquid chromatography or other equivalent chromatographic techniques, or by careful recrystallization.

The conversion to the desired salt of a physiologically acceptable cation may be accomplished by conventional techniques.

Preparation of Dihydrochalcones Having Phosphonate Substituents

The materials of General Formula Ib may be prepared according to the general scheme

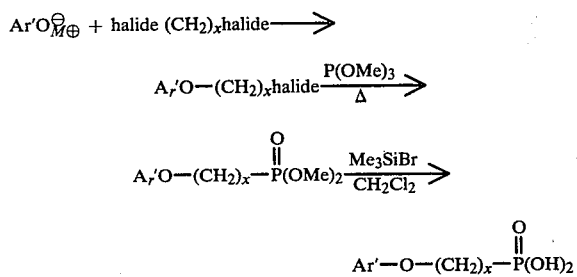

where Ar' represents a dihydrochalcone depicted in General Formula I in which R' is H and substitution occurs at the 4-position.

Any suitable dihalide may be employed with the dibromide and $x=3$ preferred. The preparative scheme may be shown as follows where X and R have the meanings given above and Y is a protective group such as benzyl.

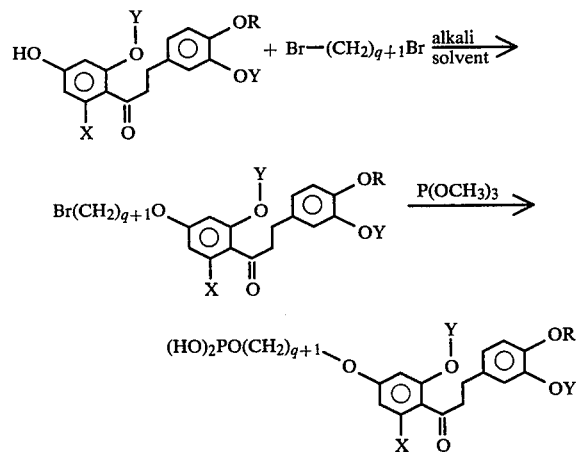

As with the preparation of those ketocarboxylic acid salts shown in Formula Ia, the phosphonate compounds conforming to Formula Ib may be prepared by combining an appropriate dihaloalkane with the appropriate dihydrochalcone in a suitable reaction medium, such as polar, aprotic liquid. The hydroxy groups, other than those at the 4-position in the dihydrochalcone, are protected with benzyl or other suitable groups to avoid unwanted reactions from occurring, particularly those with $(CH_3)_3SiBr$, added in a subsequent step.

Suitable solvents or reaction media include those materials and amounts thereof set forth above for preparation of the conjugated ester. Likewise, those acid acceptors mentioned above are also suitable in this substitution reaction in moderate molar excess, that is, the ratio of acid acceptor to dihydrochalcone is on the order of 1.25 to 4 and preferably 1.5 to 3.

The dihaloalkane is employed substantially in excess, on a molar basis, as compared to the dihydrochalcone. The relative low cost of the dihaloalkane and ease of purification of the resulting halide intermediates permit an excess of the former to be used to shift the equilibrium in favor of the intermediate. Thus, a ratio of dihaloalkane to dihydrochalcone in the range of 2 to 25 is suitable and a preferred range is 4 to 15.

The reaction is carried out at temperatures within the ranges mentioned above for the preparation of the conjugated esters and for an extended period of time (on the order of between 12 and 72 hours and preferably between 24 and 60 hours). The time required for approximately complete reaction varies inversely with the temperature.

The protected 4-(haloalkyl)-dihydrochalcone derivative intermediate may be recovered from the reaction mixture by a conventional workup such as dilution with water, acidification and extraction with a suitable solvent, such as ethyl acetate. The intermediate product may be further purified, is so desired, by column chromatography and/or recrystallization; however, the crude product is suitable for subsequent reaction to form the phosphonate.

The above described intermediate 4-(haloalkyl)-dihydrochalcane derivative is dissolved in a substantial molar excess of trimethyl phosphite and refluxed at the boiling point of the latter for a period of between 12 and 72 hours, preferably between 24 and 48 hours. Residual $P(OCH_3)_3$ is removed by vacuum distillation and the remaining protected 4-(dimethylphosphoralkoxy)dihydrochalcone derivative is puridied by conventional techniques such as extraction with a suitable solvent as, for example, ethyl acetate, followed by column chromatography and, optionally, subsequent recrystallization.

The conversion of the protected dimethylphosphonate ester to the corresponding phosphonic acid is accomplished by dissolving the ester in anhydrous solvent such as $CH_2Cl_2$ and adding dropwise over several hours, while stirring, bromotrimethylsilane. An excess of $(CH_3)_3SiBr$ is added, based on the starting phosphonate ester. A molar ratio of the former to the latter suitably being in the range of 1.25 to 8 and preferably 1.5 to 6. The $(CH_3)_3SiBr$ is added over a period of from approximately 1 to 8 hours, preferably 1 to 5 hours, at a temperature maintained at or preferably below room temperature. The most preferred temperature being 0° C. Hydrolysis is then completed by addition of a suitable solvent system for the material, containing a small amount of water. Such a system is a mixture of approximately equal parts of tetrahydrofuran and an alcohol such as ethyl alcohol, and less than 20% of the amount of either solvent, of water.

The crude protected phosphonic acid is then treated with molecular hydrogen, at pressures moderately above atmospheric, over a suitable heterogeneous catalyst, for example Pt or Pd, to reductively cleave the protective groups and yield the phosphonic acid with free hydroxy groups. The reaction mixture is then filtered and solvent removed in vacuo.

The free acid is converted to the "metal" hydrogen salt (the mono acid) by dissolving the acid in a dilute alkaline solution of a physiologically acceptable cation, such as those described above. Such solutions would most often be of the hydroxides of the physiologically acceptable cations in concentrations ranging from about 2% to 15% by weight. The resulting solution is then extracted with a suitable solvent such as ether, methylene chloride or chloroform, and a dilute solution of a mineral acid is added to adjust the pH to approximately 5. The material which precipitates on standing is filtered. Further purification by conventional techniques, such as high pressure liquid chromatography, may be used to produce a pure product.

The starting flavanones employed in the earlier described scheme include hesperetin and its X and R' substituted equivalents. Hesperetin (X=OH, R=CH$_3$) is available commercially. The other flavanones are less common and generally are prepared. One preparative route for these flavanones involves condensation of an appropriately protected hydroxyacetophenone with an appropriately protected 3-hydroxy-4-alkoxybenzaldehyde in the presence of base to give a chalcone which is then converted to the desired flavanone by treatment with strong acid.

This route may be shown as follows:

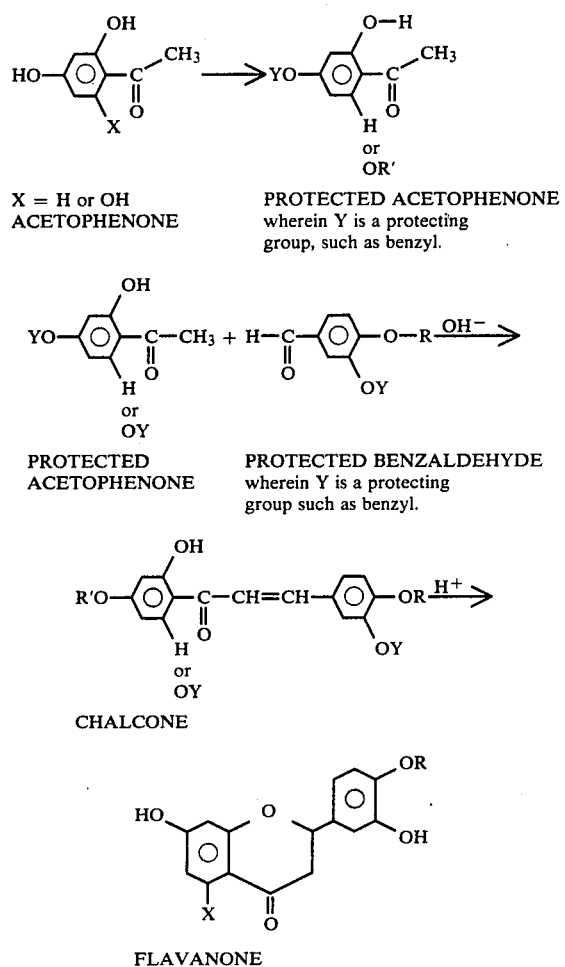

These steps can be carried out with process conditions and reagents known to those skilled in the art.

The protected hydroxyacetophenone derivatives, such as 2-hydroxy-4,6-dibenzoyloxyacetophenone and 2-hydroxy-4-benzyloxyacetophenone, are prepared from the requisite commercially available hydroxyacetophenones by treatment with a reagent such as a benzyl halide, particularly benzyl bromide or iodide or chloride (1.00–1.25) equivalent based upon the number of hydroxyl groups to be reacted) at 25°–80° C. in polar aprotic liquid phase media. Suitable media include N,N-dimethylformamide (DMF), dimethyl sulfoxide, hexamethylphosphoramide, and the like. An acid acceptor; such as a metal bicarbonate, carbonate, or hydroxide, especially an alkali metal such as K+ of a bicarbonate, carbonate or hydroxide, is also added to the reaction mixture in an amount of from 1.0 to 1.5 equivalents per mole of hydroxyl group being protected. Generally, long reaction times, such as at least 12 hours, are employed with these mild conditions. The most preferred method for preparing the protected hydroxyacetophenones involves the use of benzyl chloride (1.1 equivalent) and K$_2$CO$_3$ (1.0 equivalent) in DMF at 25°–40° C. Under these conditions the reactions are complete within 3–4 days, with product isolation being carried out by means of a standard aqueous workup.

The protected 4-alkoxy-3-hydroxybenzaldehydes, needed for condensation with the protected hydroxyacetophenones, are prepared by a two-step process from 3,4-dihydroxybenzaldehyde (protocatechualdehyde, commercially available). The first step, which is the preparation of the intermediate 4-alkoxy-3-hydroxybenzaldehydes, involves the treatment of the dihydroxybenzaldehyde with 1.0–1.1 molar equivalents of a 1-3 carbon alkyl halide (especially iodide) in a polar aprotic solvent, such as DMF, at room temperature or slightly above (15°–40° C.). An acid acceptor, such as an alkali metal carbonate, bicarbonate or hydroxide and preferably K$_2$CO$_3$, in a molar amount about equal to the moles of alkyl halides is required for this reaction. When carried out under these mild conditions, the hydroxyl group at the 4-position, being somewhat more reactive than the hydroxyl group at the 3-position, is alkylated almost exclusively. Protection of the remaining hydroxyl is then effected preferably by benzylation such as at 25°–50° C. with either benzyl chloride or benzyl bromide in DMF or a similar solvent containing 1.0–1.2 molar equivalents of K$_2$CO$_3$. This completes the preparation of the 4-alkoxy-3-benzyloxybenzaldehydes or their otherwise protected equivalents.

The aldol condensation of the protected hydroxyacetophenones with the 4-alkoxybenzaldehydes, to afford a chalcone, is best carried out with a slight molar excess (preferably 1.1 to 1.5 molar equivalents, basis acetophenone) of benzaldehyde in a lower alkanol (methanol, ethanol, isopropanol) at room temperature to 75° C. A large excess (10–20 molar equivalents) of a strong base, such as NaOH, KOH, NeOEt, or t-BuOK, is needed in order for the reaction to proceed at a reasonable rate. The preferred method for conducting this aldol condensation is to utilize about 1.25 molar equivalents of the benzaldehyde and about 15 molar equivalents of 60% KOH in absolute ethanol (10–15 ml/mmol of acetphenone) at 20°–30° C. Under these conditions, the condensation is complete within 72 hours. The chalcone products may be isolated, after neutralization of the reaction mixture, by a standard aqueous workup. Purification is carried out by recrystallization, with ethanol being the preferred solvent.

The chalcones, when protected as preferred with benzyl groups, undergo debenzylation with concomitant cyclization to the flavanones upon treatment with excess very strong mineral acid. Aqueous HI or HBr (10–20 molar equivalents) in glacial acetic acid (20–60 ml/mmol of chalcone) are preferred acids and are employed at mildly elevated temperatures (30°–100° C.). In general, these reactions proceed rather poorly with other mineral acids, such as HCl, $H_2SO_4$, or $HClO_4$. The final flavanones are isolated, as a mixture with the resulting benzyl halide co-product, by a standard aqueous workup. Purification is best accomplished by chromatographic techniques, such as thin layer chromatography or column chromatography. All of these reactions may be advantageously carried out with stirring and under an inert gas atmosphere.

The dihydrochalcone products of this invention are sweet. They may be used as non-sucrose sweeteners for edibles such as foods, medicaments and beverages. In this use they may be admixed such as by dissolving or dry mixing with the edible as is appropriate. They exhibit a sweetness substantially greater than sucrose; for instance, 2, 3', 6-trihydroxy-4-(2-oxo-3-carboxypropoxy)-4'-methoxydihydrochalcone sodium salt and 2,3',6-trihydroxy-4-(3-phosphopropoxy)-4'-methoxydihydrochalcone potassium salt demonstrate a sweetness of about 310 and 280, respectively, times that of sucrose. Thus they should be used in an amount about 1/100–1/1000 that of sucrose. Amounts of from about 0.2 to 0.005% by weight (basis edibles) may be employed. In addition, these compounds develop a maximum perceived taste intensity quickly and have little and favorable aftertastes whem compared to other synthetic sweeteners and sucrose.

The present invention will be further shown by the following preparations and examples. These are intended to exemplify the invention and are not to be construed as limiting its scope.

EXAMPLES AND PREPARATIONS

In these Examples and Preparations, the following general conditions apply: All temperatures are in degrees centigrade.

Infrared spectra were recorded on a Perkin Elmer Model 137 spectrophotometer. Proton magnetic resonance spectra were recorded on a Varian Associates T-60A spectrometer (60 MHz) and are recorded in parts per million from tetramethylsilane on the δ scale. Data are reported as follows: chemical shift, multiplicity (s=singlet, d=doublet, t=triplet, q=quartet, m=multiplet, br=broad), coupling constant (Hz), integration, and interpretation. Ultraviolet spectra were recorded on a Varian Associates Cary 118 Spectrophotometer. Melting points were determined on a Fisher-Johns melting point apparatus.

High-pressure liquid chromatography (HPLC) was performed on a Waters Associates system equipped with a Model 660 Solvent Programmer, two Model M-6000A pumps and a Schoeffel Instrument Corporation variable wavelength ultraviolet detector and a 30 cm×4 mm C-18 on μ-Bondapak column. Vapor phase chromatography (VPC) was carried out on a Varian Associates Aerograph Model 920 employing a six foot 5% SE-30 on chromosorb G column. Thin layer chromatography (TLC) was carried out on EM Laboratories pre-coated silica gel 60 F-254 plates (5×10 cm).

Diethyl ether, hexane, ethylacetate, chloroform and methylene chloride used were reagent grade solvents from J. T. Baker Chemical Company. Triethylamine was distilled from phosphorous pentoxide and stored over activated molecular sieves 4A. Dimethylformamide (DMF) was distilled from calcium hydride and stored over activated molecular sieves 4A.

PREPARATION OF PRECURSORS

Ethyl 3-methoxy-4-iodocrotonate
(ethyl-3-methoxy-4-iodo-2-butenoate)

Two grams of amberlyst 15 ion exchange resin was added to a solution of 8.23 g (0.05 mol) of ethyl 4-chloroacetoacetate in 25 mL of methyl orthoformate. The solution was stirred overnight, the resin was filtered, and excess ortho ester was removed in vacuo. The residue was then heated slowly over 1 h to 190° C., after which it was allowed to cool and then short path distilled to yield 7.37 g (83%) of ethyl 3-methoxy-4-chlorocrotonate as a colorless liquid: bp 145°–148° C. (40 mm); VPC (6 ft 5% SF 96 on 60–80 mesh chromosorb G; 160° C.; 60 cm$^3$/min He flow) $t_R$=1.9 min; NMR (CDCl$_3$) 1.10 (t, 3H, J=7 Hz, COOCCH$_3$), 3.73(s, 3H, OCH$_3$), 4.20 (q, COOCH$_2$C, J=7 Hz, COOCH$_2$C), 4.67 (s, 2H, ClCH$_2$), 5.17 (s, 1H, CH).

Fifteen grams (0.1 mol) of NaI was added to a solution of 3.58 g (0.02 mol) of ethyl 3-methoxy-4-chlorocrotonate in 150 mL of acetone. The solution was stirred vigorously for 20 h in a flask protected from light and standard workup yielded 5.38 g (100%) of ethyl 3-methoxy-4-iodocrotonate as an amber liquid: VPC (6 ft 5% SF96 on 60–80 mesh chromosorb G; 160° C.; 60 cm$^3$/min He flow) $t_R$=4.0 min; NMR (CDCl$_3$)δ1.31 (t, 3H, J=7 Hz, COOCCH$_3$), 3.73 (s, 3H, OCH$_3$), 4.24 (q, 2H, J=7 Hz, COOCH$_2$C), 4.48 (s, 2H, CH$_2$I), 5.13 (s, 1H, CH).

Flavanones by Condensing Aldehydes and Acetophenones

A. Preparation of Unprotected Aldehyde Reactants (1) A solution of 2.76 g (20.0 mmoles) of 3,4-dihydroxybenzaldehyde and 2.76 g (20.0 mmoles) of anhydrous potassium carbonate and 3.45 g (22.0 mmoles) of ethyl iodide is prepared in 15 ml of dry DMF and stirred under argon for 24 hours at room temperature. The reaction mixture is poured into 50 ml of water, saturated with sodium chloride and extracted thrice with diethyl ether. The ether extracts are washed with water, and brine, dried and concentrated to yield the ethoxyaldehyde as dark crystals.

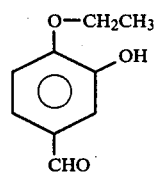

(2) The reaction is repeated using 3.74 g (22.0 mmoles) of n-propyl iodide in place of ethyl iodide to yield the propoxyaldehyde

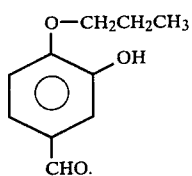

(3) The reaction is repeated using 3.12 g (22.0 mmoles) of methyl iodide in place of ethyl iodide to yield the methoxyaldehyde.

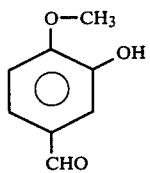

B. Preparation of 4-Alkoxy-3-benzyloxybenzaldehyde

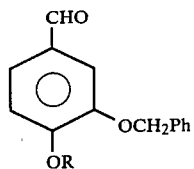

(R = 1-3 carbon alkyl)

4-Alkoxy-3-hydroxybenzaldehyde (1.0 equiv.), benzyl chloride (1.2 equiv.), and $K_2CO_3$ (1.2 equiv.) are stirred in anhydrous DMF at 35° C. for 72 hours. The reaction is poured into ether and the resulting mixture washed thoroughly with $H_2O$, dilute aqueous KOH (until the ethered solution is free of unreacted hydroxybenzaldehyde as determined by TLC), $H_2O$ again, and finally brine. Evaporation affords crude 4-alkoxy-3-benzyloxybenzaldehyde which is generally suitable for use, as is, in the condensation reaction. Additional purification may be achieved by silica gel column chromatography.

C. Preparation of Protected Acetophenones (1) Preparation of 2-Hydroxy-4,6-dibenzyloxyacetophenone

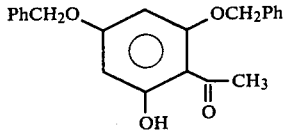

2,4,6-Trihydroxyacetophenone (16.8 g, 0.10 mol, Aldrich Chemical Company) and benzyl chloride (27.8 g, 0.22 mol) were dissolved in 200 ml of dry DMF and the solution was thoroughly purged with argon. The mixture was treated with 27.6 g (0.20 mol) of $K_2CO_3$ and stirred at 35° C. for 84 hours. The reaction was poured into ether (1200 ml) and resulting mixture washed with $H_2O$ (1×500 ml), 5% aqueous KOH solution (3×500 ml), $H_2O$ (1×500 ml), and saturated NaCl solution (1×250 ml). After drying over $MgSO_4$, the ethereal solution was evaporated to afford 27.4 g of crude product as an off-white granular solid. Trituration of the crude product with ether (100 ml), followed by filtration and drying in vacuo provided 13.5 g (38.8%) of 2-hydroxy-4,6-dibenzyloxyacetophenone as a white solid, mp 101°-102° C., i.e.,

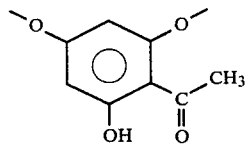

wherein R' is benzyl. The product was homogeneous by silica gel TLC ($CHCl_3$ elution) and the assigned structure was verified by both NMR and elemental analysis.

(2) Preparation of 2-hydroxy-4-benzyloxyacetophenone

The reaction of (1) above is repeated using 1.1 molar equivalents of benzyl chloride, 1.0 molar equivalent of $K_2CO_3$, and substituting for the above acetophenone 2,4-dihydroxyacetophenone

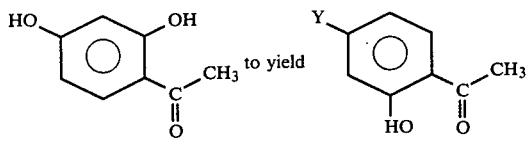

D. Preparation of 2-Hydroxy-3',4,6-tribenzyloxy-4'-alkoxychalcone

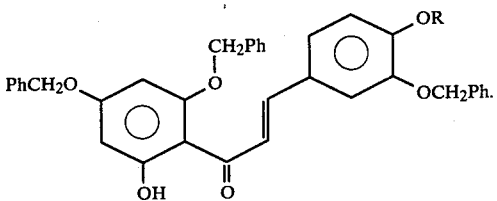

(R = 1-3 carbon alkyl)

A 500-ml, 3-neck flask, equipped with overhead stirrer, is charged with 9.04 g (25.9 mmol) of 2-hydroxy-4,6-dibenzyloxyacetophenone, 1.25 equiv. (32.4 mmol) of 4-alkoxy-3-benxyloxybenzaldyde, and 300 ml of absolute ethanol. The mixture is stirred until a homogeneous solution is obtained, at which point 26.4 g (0.39 mol) of powdered sodium ethoxide is added. The reaction is stirred at room temperature under argon for 72 hours and then quenched by the addition of 39 g (0.65 mol) of glacial acetic acid.

The reaction mixture is evaporated to complete dryness and triturated for 30 minutes with 500 ml of boiling tetrahydrofuran and filtered. The trituration is repeated twice, and the combined filtrates are evaporated to dryness. Recrystallization from boiling toluene affords chalcone (40-65%) as a bright yellow crystalline solid. The identity and homogeneity of the product are determined by silica gel TLC (ethyl acetate-hexane, 1:1), proton NMR, and elemental analysis.

E. Preparation of 3′,5,7-Trihydroxy-4′-alkoxyflavanone

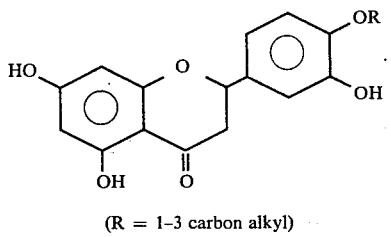

(R = 1–3 carbon alkyl)

A 1.0 mmol sample of 2-hydroxy-3′,4,6-tribenzyloxy-4′-alkoxychalcone is dissolved in 40 ml of glacial acetic acid at 60° C. and treated with 2 ml of 48% aqueous HBr. The yellow solution becomes deep reddish-orange upon addition of the acid. After stirring 24 hours at this temperature, the reaction is poured into $H_2O$ (200 ml) and the resulting aqueous mixture extracted with an equal volume of ethyl acetate. The organic extract is washed with $H_2O$ (2×100 ml), 5% aqueous $NaHCO_3$ solution (2×100 ml), $H_2O$ (1×100 ml), saturated aqueous NaCl solution (1×50 ml), and dried over $MgSO_4$. Evaporation affords the crude flavanone admixed with three equivalents of benzyl bromide.

Silica gel column chromatography (elution with ethyl acetate-hexane, 1:1) affords flavanone (30–60%) as an off-white crystalline solid, which may be further purified by recrystallization. Product identity and homogeneity are determined by silica gel TLC (ethyl acetate-hexane, 1:1), proton NMR, and elemental analysis.

F.

The coupling, exemplified by parts D and E, is repeated four more times varying the aldehyde among the three materials of Part A of this preparation and the two acetophenones of Part B so, with the materials of D and E, as to yield the six possible flavanones of General Formula II which can result when X is H or OH and R is $CH_3$, $C_2H_5$ of $C_3H_7$. The compound in which X equals OH, and R equals $CH_3$ is the flavanone hesperetin, which is available commercially, as well.

EXAMPLE 1

Preparation of 2,3′,6-Trihydroxy-4-(2-oxo-3-carboxypropoxy)-4′-methoxydihydrochalcone Sodium Salt One-hundred milliliters of N,N-dimethylformamide (DMF) was added to a mixture of 6.04 g (20 mmol) of hesperetin, 3.04 g (22 mmol) of $K_2CO_3$, and 5.40 g (20 mmol) of ethyl 3-methoxy-4-iodocrotonate. The resultant mixture was stirred at 0° C. for 16 hours in a flask protected from light, followed by 5 days at ambient temperature, after which standard workup yielded 9.92 g of crude 3′,5-dihydroxy-4′-methoxy-7-[(2-methoxy-3-carbethoxyprop-2-enyloxy]flavanone as a dark oil. Without purification, the crude material was dissolved in 95 mL of $CH_3OH$ and treated with 5 mL of 50% $H_2SO_4$ at reflux for 2.5 hours. Standard workup, followed by column chromatography over 775 g of silica gel ($CHCl_3$—$CH_3OH$) and recrystallization (hexane-EtOAc), yielded 1.82 g (20%) of 3′,5-dihydroxy-4′-methoxy-7-(2-oxo-3-carbomethoxypropoxy) flavanone as tiny clusters: mp 114°–118° C.; IR (KBr) 2.90 (OH), 5.72 (ester C=O), 5.82 (ketone C=O), 6.11 (ketone C=O) $\mu$m; UV (MeOH)$\lambda_{max}$ 286 nm ($\epsilon$ 21500); NMR (acetone-d$_6$)$\delta$ 2.45–3.26 (br m, 2H, ArCOCH$_2$), 3.70 (s, 3H, COOCH$_3$) 3.86 (s, 3H, Ar′OCH$_3$), 4.60 (s, 2H, ArOCH$_2$), 5.00 (s, 2H, ArOCCOCH$_2$), 5.33–5.63 (m, 1H, Ar′CHO), 6.06 (s, 2H, ArH), 7.02 (m, 3H, Ar′H). Anal. ($C_{21}H_{20}O_9$) C, H.

The purified flavanone (833 mg, 2.0 mmol) was hydrogenated over 0.4 g Pd/C at 1 atm for 48 hours as a solution in 85 mL of 10% KOH. Standard workup, followed by recrystallization ($H_2O$—$CH_3OH$), yielded 519 mg (64%) of the substituted dihydrochalcone as light tan needles: mp 227°–228° C. dec; IR (KBr) 3.0–4.4 (OH), 5.80 (carboxylic acid C=O), 5.85 (aliphatic ketone C=O), 6.19 (aromatic ketone C=O) $\mu$m; UV (MeOH)$\lambda_{max}$ 224 nm ($\epsilon$ 22600), 285 (23500); NMR (acetone-d$_6$) 2.84 (t, 2H, J=7 Hz, ArCOCCH$_2$Ar′), 3.37 (t, 2H, J=7 Hz, ArCOCH$_2$CAr′), 3.60 (s, 3H, Ar′OMe), 4.65 (s, 2H, ArOCH$_2$), 6.04 (s, 2H, ArH). Anal. ($C_{20}H_{20}O_9$) C, H. A 189-mg sample of 2,3′,6-trihydroxy-4-(2-oxo-3-carboxypropoxy)-4′-methoxydihydrochalcone was titrated to the sodium salt by the general method to yield 200 mg of the sodium salt as a flocculent white solid.

Preparation of 2,3′,6-Trihydroxy-4-(3-phosphopropoxy)-4′-methoxydihydrochalcone mono-Potassium Salt A mixture of 2.37 g (5 mmol) of 2,3′,6-tris(benzyloxy)-4-hydroxy-4′-methoxydihydrochalcone, 1.38 g (10 mmol) of $K_2CO_3$, and 70.1 g (50 mmol) of 1,3-dibromopropane in 75 mL of DMF was reacted for 48 hours, after which standard workup yielded 2.91 g (84%) of 2,3′,6-tris(benzyloxy)-4-(3-bromopropoxy)-4′-methoxydihydrochalcone as a white solid. The resulting intermediate bromide (2.91 g, 4.18 mmol) was dissolved in 50 mL of $P(OCH_3)_3$ and refluxed for 39 hours. After all solvent was removed in vacuo, standard workup, followed by column chromatography over 200 g of silica gel ($CHCl_3$—$CH_3OH$), yielded 1.93 g (64%) of 2.3′,6-tris(benzyloxy)-4-(dimethyl-3-phosphopropoxy)-4′-methoxydihydrochalcone as an oil, which crystallized on standing. Crystallization from hexane-EtOAc yielded colorless clusters: mp 92°–95.5° C.; IR (film) 5.88 (C=O) $\mu$m; UV (MeOH)$\lambda_{max}$ 278 nm ($\epsilon$ 7600); NMR (CDCl$_3$)$\delta$ 2.90 (m, 4H, ArCOCH$_2$CH$_2$Ar′), 3.64 [s, 6H, PO(OCH$_3$)$_2$], 3.77 (s, 3H, Ar′OCH$_3$), 3.94 (t, 2H, J=6 Hz, ArOCH$_2$), 5.03 (s, 6H, PhCH$_2$O), 6.17 (s, 2H, ArH), 7.37 (s, 15H, PhH). Anal ($C_{42}H_{45}O_9P$) C, H.

To a solution of 725 mg (1 mmol) of the dimethyl phosphonate ester in 10 mL of $CH_2Cl_2$ was added 337 mg (2.2 mmol) of Me$_3$SiBr while stirring at 0° C. After 30 min, 2.2 mmol of additional Me$_3$SiBr was added and stirring continued at 0° C. for 2 hours, at which point the hydrolysis reaction was quenched by the addition of 60 mL of THF-$H_2O$-EtOH (5:1:6). The crude tribenzylphosphonic acid was then hydrogenated over 300 mg of Pd/C at 3 atm for 15 hours. The reaction mixture was then filtered through Celite and concentrated in vacuo to give a tan solid. The solid product was dissolved in 25 mL of 5% KOH and washed with Et$_2$O, after which the pH was adjusted to 5.0 by the addition of 10% HCl. After the solution was left standing overnight, filtration yielded 316 mg of an impure crystalline product. Preparative HPLC of this sample then yielded 217 mg (51%) of the K salt as a flocculent white solid: mp 138–150 dec; IR (KBr) 2.96–4.22 (OH), 6.17 (C=O) $\mu$m; UV (MeOH)$\lambda_{max}$ 225 nm ($\epsilon$ 18,800), 287 (23,100);

NMR (CD₃OD)δ 2.83 (t, 2H, J=6 Hz, ArCOCCH₂Ar'), 3.30 (t, 2H, J=6 Hz, ArCOCH₂), 3.80 (s, 3H, Ar'OCH₃), 4.05 (t, 2H, J=6 Hz, ArOCH₂), 5.95 (s, 2H, ArH). Anal. (C₁₉H₂₂KO₉P.1.5H₂O) C, H.

Other salts may be formed by varying the base among NaOH, Ca(OH)₂ and the like, or by passage of a solution of the dihydrochalcone over a strong acid ion exchange resin followed by titration with the desired metal hydroxide, or often by merely adding an excess of the desired cation to a solution of dihydrochalcone and precipitating the desired salt. In a typical preparation, a solution of the potassium salt is passed over a freshly washed and regenerated bed of the acidic ion exchange resin Amberlite 120 (Rohm and Haas) in the acid form. This forms the free acid. The solution of free acid may then be separated into several parts, each of which is neutralized. Thus, by addition of one equivalent of Ca(OH)₂, NaOH, or Mg(OH)₂, the salts of Ca, Na and Mg may be formed.

While in the foregoing specification a detailed description of the present invention has been set forth, including reference to specific embodiments, this is for the purpose of illustration and is not intended to limit in any way the present invention. Thus, without departing from the spirit and scope of the instant invention, alternate and additional modifications may be made to the above described embodiments as would be apparent to those skilled in the art.

What is claimed is:

1. A dihydrochalcone compound represented by the structural formula

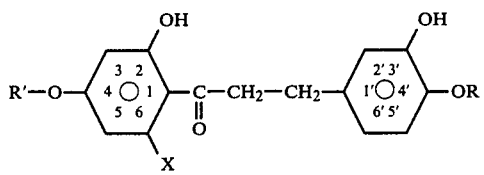

wherein R' is

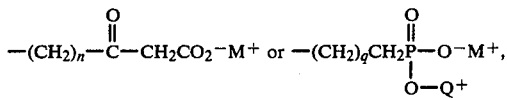

n and q, respectively, are numbers between 1 and 5, R is a lower alkyl of from 1 to 3 carbon atoms, X is hydrogen or hydroxy, and M⁺ and Q⁺ are the same or different and are physiologically acceptable cations.

2. The dihydrochalcone compound of claim 1, wherein n and q are each 1 to 3.

3. The dihydrochalcone compound of claim 2, wherein R' is

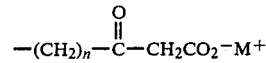

and n is 1.

4. The dihydrochalcone of claim 3, wherein R is methyl, ethyl or normal-propyl and M⁺ is Na⁺, K⁺, ½Ca⁺⁺ or ½Mg⁺⁺.

5. The dihydrochalcone compound of claim 4, wherein X is hydroxy.

6. The dihydrochalcone compound of claim 4, wherein R is methyl.

7. The dihydrochalcone compound of claim 4, wherein M⁺ is Na⁺ or K⁺.

8. The dihydrochalcone compound of claim 4, wherein n is 1, X is hydroxy, R is methyl and M⁺ is Na⁺.

9. The dihydrochalcone compound of claim 2, wherein R' is

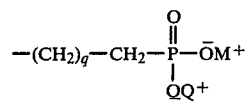

and q is 2.

10. The dihydrochalcone compound of claim 9, wherein R is methyl, ethyl or normal-propyl and M⁺ and Q⁺ are H⁺, Na⁺, K⁺, Ca⁺⁺, ½Ca⁺⁺, Mg⁺⁺ or ½Mg⁺⁺.

11. The dihydrochalcone compound of claim 9, wherein X is hydroxy.

12. The dihydrochalcone compound of claim 9, wherein R is methyl.

13. The dihydrochalcone compound of claim 9, wherein M⁺ is K⁺ and Q is H⁺.

14. The dihydrochalcone compound of claim 9, wherein q is 2, X is hydroxy, R is methyl, M⁺ is K⁺ and Q⁺ is H⁺.

* * * * *